(12) United States Patent
Maneg et al.

(10) Patent No.: US 11,325,964 B2
(45) Date of Patent: May 10, 2022

(54) PROCESS FOR PREPARING IMMUNOGLOBULIN COMPOSITIONS

(71) Applicant: Biotest AG, Dreieich (DE)

(72) Inventors: Oliver Maneg, Bad Homburg (DE); Achim Hannappel, Frankfurt am Main (DE); Alexander Moehlenkamp-Roettger, Floersheim-Wicker (DE); Wolfgang Moeller, Oberursel (DE); Dieter Rudnick, Dreieich (DE)

(73) Assignee: BIOTEST AG, Dreieich (DE)

( * ) Notice: Subject to any disclaimer, the term of this patent is extended or adjusted under 35 U.S.C. 154(b) by 350 days.

(21) Appl. No.: 16/320,900

(22) PCT Filed: Jul. 26, 2017

(86) PCT No.: PCT/EP2017/068914
§ 371 (c)(1),
(2) Date: Jan. 25, 2019

(87) PCT Pub. No.: WO2018/019898
PCT Pub. Date: Feb. 1, 2018

(65) Prior Publication Data
US 2019/0161533 A1 May 30, 2019

(30) Foreign Application Priority Data

Jul. 27, 2016 (EP) ..................... 16181493

(51) Int. Cl.
*C07K 16/06* (2006.01)
*C07K 1/30* (2006.01)
*C07K 1/22* (2006.01)
*G01N 33/68* (2006.01)

(52) U.S. Cl.
CPC .............. *C07K 16/065* (2013.01); *C07K 1/22* (2013.01); *C07K 1/30* (2013.01); *G01N 33/68* (2013.01); *C07K 2317/94* (2013.01)

(58) Field of Classification Search
CPC .................................. C07K 1/22; C07K 1/30
See application file for complete search history.

(56) References Cited

U.S. PATENT DOCUMENTS

| 4,296,027 | A | 10/1981 | Condie | |
|---|---|---|---|---|
| 5,854,051 | A | 12/1998 | Chandrashekar et al. | |
| 2001/0051708 | A1* | 12/2001 | Laursen | A61P 43/00 |
| | | | | 530/387.1 |
| 2012/0294847 | A1* | 11/2012 | Mintz | A61P 31/00 |
| | | | | 424/130.1 |
| 2013/0058961 | A1* | 3/2013 | Teschner | A61P 37/06 |
| | | | | 424/177.1 |
| 2013/0245139 | A1* | 9/2013 | Kozlov | C08F 220/585 |
| | | | | 521/27 |
| 2016/0244512 | A1* | 8/2016 | Teschner | B01D 61/142 |
| 2017/0015732 | A1* | 1/2017 | Park | C07K 16/065 |
| 2017/0073396 | A1 | 3/2017 | Bataille et al. | |

FOREIGN PATENT DOCUMENTS

| AU | 2013206196 | 6/2013 |
|---|---|---|
| SU | 1137098 | 1/1985 |
| WO | 99/10009 | 3/1999 |
| WO | 2013/006449 | 1/2013 |
| WO | 2015/136217 | 9/2015 |

OTHER PUBLICATIONS

Amersham Biosciences, "Ion Exchange Chromatography: principles and methods" pp. 1-163 (Year: 2002).*
Tanaka et al. "High quality human immunoglobulin G purified from Cohn fractions by liquid chromatography" Brazilian J. of Medical and Biological Research , 33, 27-30 (Year: 2000).*
International Search Report & Written Opinion dated Oct. 6, 2017, for corresponding International Application No. PCT/EP2017/068914.
Extended European Search Report dated Nov. 9, 2016, for correspondence European Application No. 16181493.4.
Anonymous, "Novel Recombinant Monoclonal Antibodies ABFINITY (tm) Technology Ensures Performance," BioProbes (2009).
Pensky et al., "Properties of Highly Purified Human Properdin." (1968) The Journal of Immunology 100(1):142-158.
Office Action dated Oct. 20, 2021, for corresponding Chinese Application No. 201780052839.1.
Office Action dated Aug. 30, 2021, for corresponding Eurasian Application No. 201990392.
Office Action dated Sep. 8, 2021, for corresponding Japanese Application No. 2019-504003.

* cited by examiner

*Primary Examiner* — Daniel E Kolker
*Assistant Examiner* — James L Rogers
(74) *Attorney, Agent, or Firm* — Lewis Kohn Walker LLP; David M. Kohn

(57) ABSTRACT

A process for the preparation of pharmaceutically acceptable immunoglobulin compositions from plasma-derived immunoglobulin fractions which allows the parallel preparation of immunoglobulin compositions enriched in IgG, IgM and IgA. In this process, immunoglobulin contained in Cohn fraction I/II/III or Kistler Nitschmann fraction A+I is resolubilized at conductivities of at least 1 mS/cm, and following removal of contaminating protein the resolubilized immunoglobulin is subjected to anion exchange chromatography to obtain IgG- and IgM/IgA-enriched immunoglobulin compositions. The IgG-enriched immunoglobulin composition is further subjected to treatment with a cation exchange material to obtain an immunoglobulin composition having a reduced properdin content.

29 Claims, No Drawings

PROCESS FOR PREPARING IMMUNOGLOBULIN COMPOSITIONS

The present invention relates to a process for the preparation of IgG-enriched immunoglobulin compositions and, optionally, IgM- and/or IgA-enriched immunoglobulin compositions from human plasma, to a process for reducing the properdin content in properdin-containing IgG compositions, and to an IgG-enriched pharmaceutical immunoglobulin composition.

Immunoglobulin compositions prepared from human plasma and suitable for medical use are known in the art and for several decades have played an important role in the treatment of a wide range of diseases. Immunoglobulins are used, for example, for the treatment of infections in humans and can be assigned to various classes with various biochemical and physiological properties. For example, IgG participates in defending against viral antigens, whereas IgM is predominantly active in antibacterial and antitoxin immune responses and thus is used in the prophylaxis or treatment of bacterial infections. Commercial immunoglobulin compositions, therefore, comprise IgG, IgA and IgM in various percentages, with different preparations having different treatment applications. At present, Pentaglobin® (Biotest AG, Dreieich, Germany) is the only IgM-containing immunoglobulin composition which is commercially available on the market.

Immunoglobulin compositions for medical use are usually prepared from fractions of blood plasma or serum, which are obtained by classical Cohn plasma fractionation methods or its well-known modifications, e.g. Cohn/Oncley and Kistler/Nitschmann. These fractions are then subjected to a number of purification steps to remove contaminants including viruses, denatured proteins, proteases and lipids. Human plasma for fractionation is collected from thousands of donors and may contain pathogenic viruses despite thorough testing of the source plasma. Therefore process steps to inactivate or remove viruses are important in order to obtain safe products for medical use. Several techniques for virus inactivation/removal are known in the art, e.g. chemical or heat treatments, irradiation with UVC light or nanofiltration, which are performed in order to ensure overall virus safety.

In addition to viruses which are potentially present, it is also important to remove other contaminants like proteolytic enzymes, vasoactive substances such as prekallikrein activator, protein aggregates and denatured immunoglobulins, to achieve a well-tolerated product. Denatured immunoglobulins and immunoglobulin aggregates are a potential risk for the patients because they have a high capacity to activate complement unspecifically, leading to severe side effects in patients receiving these denatured immunoglobulins. The capacity of an immunoglobulin composition for unspecific activation of the complement system is related to its anticomplementary activity (ACA), which is the ability of a protein composition to consume complement in a complement assay, and can be measured by standardized test methods, for example a method as described in the European Pharmacopoeia 8.0 (2.6.17—Test for Anticomplementary Activity of Immunoglobulin), according to which the acceptance limit for ACA is <1 CH50/mg protein.

The removal of all these contaminants is important (1) in order for the product to be tolerated by the patient after intravenous administration, (2) to ensure the product complies with bio-safety guidelines regarding viral contamination, (3) to allow the product to be stable during long-term storage, and (4) to generate the desired compound mixture/pharmaceutical composition.

Processes for the production of IgG-, IgM- and/or IgA-enriched immunoglobulin compositions have been disclosed in the prior art.

EP 0 447 585 A1 describes the production of intravenously tolerable polyclonal IgG solutions which shall be free of aggregates, vasoactive substances and proteolytic activity. Starting from Cohn fractions II or II/III and following a treatment with octanoic acid to precipitate contaminating protein, the obtained solution is subjected to cation exchange chromatography to remove IgG-aggregates which may be present in Cohn fractions II or II/III in amounts up to 5%. Cation exchange chromatography may be carried out under conditions where IgG is bound to the cation exchange material or in a flow-through mode.

EP 0 825 998 A describes the production of pharmaceutically acceptable IgG preparations starting from Cohn fractions II or supernatant fraction III. In order to eliminate anticomplementary activity and to inactivate virus, the fractions are treated with pepsin and subjected to solvent/detergent treatment. Chemicals and pepsin used for virus inactivation are removed by treatment with a cation exchanger.

US 2013/0058961 A1 describes methods for reducing the anticomplementary activity in a plasma-derived immunoglobulin composition comprising IgG, wherein suspended plasma fraction precipitates selected from Cohn fraction precipitates and Kistler-Nitschmann precipitates are contacted with a cation exchange resin under a first solution condition comprising a pH of no more than 6.0 and a conductivity of no more than 11 mS/cm to bind the IgG immunoglobulins and a first amount of ACA to the cation exchange resin, and wherein the IgG immunoglobulins are eluted from the cation exchange resin by contacting the cation exchange resin with an elution buffer comprising a pH of at least 7.5 and a conductivity of at least 15 mS/cm to form an eluate comprising a leading portion comprising no more than 80% of the eluate having a reduced ACA and containing the IgG. The described methods do not involve the recovery of immunoglobulin compositions comprising IgM and IgA.

WO 98/05686 A discloses a method for the purification or recovery of IgG from plasma material, wherein the plasma material is subjected to chromatographic fractionation on a macroporous anion exchange resin to remove contaminating protein, in particular transferrin, and IgM. The desired IgG is obtained in the flow-through from the anion exchange resin. Cohn supernatant I delipidated by adsorption to finely divided silicon dioxide or solubilized Cohn fractions II+III are used as the starting material to obtain purified IgG.

U.S. Pat. No. 4,136,094 A discloses the preparation of intravenous IgG-containing immunoglobulin compositions, wherein human blood plasma is mixed with fumed silica to adsorb contaminating protein to stabilize the plasma product, followed by subjecting the stabilized plasma product to anion exchange chromatography and separating purified IgG. As disclosed in WO 98/05686, silica treatment results in a reduction of $IgG_3$. A natural IgG subclass distribution, however, is mandatory for state-of-the-art, commercial IgG preparations.

Related U.S. Pat. No. 4,296,027 A discloses that precursors of the fibrinolytic, coagulation and kininogen systems such as fibrinogen, plasminogen, factor XII, prekallikrein system and complement components are removed from blood plasma by the silica dioxide treatment. While properdin was found to be part of the removed protein and was not detected in the treated crude plasma, the final IgG compositions were not tested for their properdin content and the role of this molecule for the usefulness of intravenous immunoglobulin preparations was not discussed.

WO 2011/080698 A describes a process for the preparation of intravenous IgG compositions by subjecting human plasma or a plasma product enriched in IgG to cation exchange chromatography under conditions designed to enable the binding of IgG. Following elution the IgG solution is subjected to anion exchange chromatography for further polishing.

EP 0 413 187 A1 describes a process for the preparation of intravenous immunoglobulin solutions containing IgM, IgA and IgG in concentrated form and having an IgG subclass distribution which is close to that of normal pooled blood plasma. Starting from Cohn fraction III, these immunoglobulin solutions are obtained by subjecting the supernatant of an octanoic acid treatment to DEAE-Sephadex A-50 adsorption.

EP 0 013 901 A1 describes a method for the preparation of IgM-enriched immunoglobulin compositions starting from Cohn fraction III and including steps using octanoic acid, β-propiolactone and an adsorption step using an anionic exchange resin. This method is used to produce Pentaglobin®—to date the only commercially available intravenous IgM product. β-Propiolactone is a well-known chemical used in sterilization steps in order to inactivate viruses which are potentially present. β-Propiolactone is a very reactive substance which causes the chemical modification of proteins.

EP 0 352 500 A2 describes the preparation of an IgM concentrate for intravenous application with a reduced anti-complementary activity by using anionic exchange chromatography, β-propiolactone, UVC light irradiation and an incubation step at increased temperature (40° C. to 60° C.). The preparation produced by this method was stable in liquid solution for a limited time due to the chemical modification.

EP 0 345 543 A2 discloses a highly concentrated IgM preparation with at least 33% IgM for therapeutic use, the preparation being substantially free of isoagglutinin titres. In this patent application an octanoic acid precipitation is carried out by adding the octanoic acid, and the isoagglutinins are removed by Synsorb affinity chromatography. The final preparation had to be freeze dried.

EP 0 413 188 A1 describes the preparation of protein solutions enriched in IgM and IgG. Starting from Cohn fraction III or II/III, these methods involve subjecting a protein solution to octanoic acid treatment and anion exchange chromatography, where IgM and IgA are bound to the anion exchange resin and an IgG-enriched fraction may be obtained as a flow-through fraction.

EP 0 450 412 A describes the use of mild-heat treatment of IgM preparations at 40 to 62° C., preferably 45 to 55° C., at pH 4.0 to 5.0, to reduce the non-specific complement activation. In this patent application octanoic acid is added to a Cohn fraction III suspension in order to remove prekallikrein activator and lipoproteins by centrifugation. The heat treatment leads to partial loss of antigenic determinants of IgM. This may increase the risk of generating neo-antigens leading to an increased immunogenicity in humans or to loss of activity.

WO 2011/131786 and WO 2011/131787 disclose processes for the preparation of IgM immunoglobulin compositions starting from Cohn fraction I/III or Kistler/Nitschmann fractions B or B+I. The plasma fractions are provided as a solution comprising the immunoglobulins and are mixed with octanoic acid and treated with a vibrating agitator to precipitate contaminating protein. Precipitated protein is removed from the solution to yield the IgM containing immunoglobulin composition. The use of a vibrating agitator during the step where the immunoglobulin solution is mixed with the octanoic acid results in a higher inactivation and removal of virus particles, especially non-enveloped viruses in the course of the process. Furthermore, an improved removal of proteolytic activity is achieved in comparison to conventional stirring. IgG contained in Cohn fraction II is removed before precipitation of the starting material.

As disclosed in the prior art, processes for the preparation of IgG-enriched immunoglobulin compositions usually start from Cohn fraction II or Cohn fractions II/III, which contain most of the IgG. Cohn fraction I which contains only smaller amounts of immunoglobulins but large amounts of fibrinogen and other undesired contaminating protein is usually removed. On the other hand, IgM- and IgA-enriched immunoglobulin compositions are usually prepared starting from Cohn fraction III, which contains most of the IgM and IgA, after separation from Cohn fraction II which contains most of the IgG. Thus, the removal of undesired proteins in Cohn fraction I, such as fibrinogen, at an early manufacturing stage facilitates the preparation of IgG-containing compositions on the one side and of IgM- and IgA-containing compositions on the other side. The precipitation of Cohn fraction I, however, has several disadvantages. Specifically, the precipitation of Cohn fraction I results in loss of immunoglobulins due to carry-over of supernatant in precipitate fraction I and due to technical losses during filtration or centrifugation, where especially IgA and IgM are exposed to additional sheer stress by these filtration or centrifugation steps. Moreover, the separate filtration or centrifugation results in higher production costs due to higher labor costs and costs for equipment and consumables.

Using combined Cohn fractions I/II/III as a starting material for simultaneous preparation of IgG-, IgA and IgM-enriched immunoglobulin compositions in order to avoid loss of immunoglobulin and to improve yield in desired immunoglobulins, however, may result in problems to remove undesired immunoglobulin and contaminants and, thus, in an inacceptable ACA. In particular, the inventors observed that IgG-enriched immunoglobulin compositions obtained from Cohn fractions I/II/III or Kistler-Nitschmann fraction A+I following anion exchange chromatography still have an inacceptable high ACA.

The object of the invention is to provide an economic process for the preparation of pharmaceutically acceptable immunoglobulin compositions from blood plasma, in particular immunoglobulin compositions which meet the acceptance limit for anticomplementary activity according to the European Pharmacopoeia, wherein the process allows the parallel preparation of IgG-, IgM- and IgA-enriched immunoglobulin compositions to keep the loss of immunoglobulin from blood plasma as low as possible.

It is a further object of the invention to provide a process for reducing the properdin content in properdin-containing IgG compositions.

It is still a further object of the invention to provide a pharmaceutically acceptable IgG composition which meets the acceptance limit for anticomplementary activity according to the European Pharmacopoeia.

The present invention provides a process for the preparation of pharmaceutically acceptable immunoglobulin compositions from a plasma-derived immunoglobulin fraction comprising or consisting of Cohn fraction I/II/III or Kistler-Nitschmann fraction A+I, said process comprising the steps of:
(a) resolubilizing immunoglobulin contained in the plasma-derived immunoglobulin fraction comprising or consisting of Cohn fraction I/II/III or Kistler-Nitschmann fraction A+I by resuspending said plasma-derived immunoglobulin fraction under conditions to adjust the conductivity of the suspension to at least 1 mS/cm to obtain a suspension containing resolubilized IgG, IgM and IgA;
(b) precipitating, and optionally adsorbing, contaminating protein in the suspension obtained in step (a) and removing said contaminating protein to obtain an impurity-depleted immunoglobulin composition;
(c) subjecting the impurity depleted immunoglobulin composition obtained in step (b) to ion exchange chromatography using an anion exchange resin under conditions of pH and conductivity adjusted to substantially bind IgM and IgA and, optionally, IgG to the resin, and obtaining IgG-enriched immunoglobulin compositions in the flow-through fraction and/or by eluting IgG from the anion exchange resin under conditions where IgM and IgA remain bound to the anion exchange resin, optionally followed by eluting IgM and/or IgA from the anion exchange resin to obtain immunoglobulin compositions enriched in IgM- and/or IgA; and
(d) subjecting the IgG-enriched immunoglobulin composition obtained in step (c) to treatment with a cation exchange material under conditions of pH and conductivity where properdin is bound to said cation exchange material, and recovering IgG to obtain an IgG-enriched immunoglobulin composition having a reduced properdin content.

The term "enriched" as used in combination with specific immunoglobulins such as IgG, IgM and IgA means that the proportion of the respective immunoglobulin in such an immunoglobulin composition is enriched with respect to at least one other immunoglobulin when compared with the relative amounts of these immunoglobulins in normal blood plasma and, thus, with the relative amounts of the resolubilized immunoglobulins in the suspension obtained from plasma-derived immunoglobulin fractions comprising or consisting of Cohn fraction I/II/III or Kistler-Nitschmann fraction A+I.

According to the method of the invention, ACA in IgG-enriched immunoglobulin compositions obtained from plasma-derived immunoglobulin compositions comprising or consisting of Cohn fractions I/II/III or Kistler-Nitschmann fraction A+I is reduced, if the IgG-enriched immunoglobulin compositions obtained after anion exchange chromatography are subjected to further treatment with a cation exchange material. The inventors found that the undesired ACA in IgG-enriched immunoglobulin compositions is due to the high properdin content in Cohn fraction I and corresponding fractions of other fractionation processes, which is brought into solution under the conditions of conductivity that are necessary to resolubilize IgM and IgA in amounts required for industrial preparation processes. Properdin is a key regulatory protein in the alternative complement pathway. It is a soluble glycoprotein found in plasma at a concentration of about 25 µg/ml and is composed of several identical subunits of 53 kD binding to each other in a head to tail manner to form cyclic polymers (for Review, see, L. Kouser et al, Frontiers in Immunology, Vol. 4, Article 93, April 2013). This properdin is not removed by conventional purification steps such as octanoic acid treatment and anion exchange chromatography, as they are used in known processes for the production of IgM- and IgA-enriched immunoglobulin compositions.

The plasma-derived immunoglobulin fractions to be used as the starting material in step (a) of the process of the invention comprise or consist of Cohn fractions I/II/III or Kistler-Nitschmann fraction A+I, i.e., those fractions of conventional blood plasma fractionation processes which contain essentially all of the IgG-, IgA- and IgM-immunoglobulins in blood plasma and, as an impurity, part of the fibrinogen which is not separated by cryo-precipitation. The term "Cohn fraction I/II/III" as used herein is meant to include Cohn fractions I/II/III as obtained by the classic Cohn fractionation process as well as fractions equivalent thereto in their immunoglobulin compositions obtained by modifications of the Cohn fractionation process.

Depending on the intended use, the plasma-derived immunoglobulin fractions can be obtained from human or animal blood plasma, but typically the immunoglobulin fractions are derived from human plasma. The immunoglobulin fractions are present in a solid or semi-solid form and may contain considerable amounts of contaminating protein.

In step (a), immunoglobulin contained in the plasma-derived immunoglobulin fraction comprising or consisting of Cohn fraction I/II/III or Kistler-Nitschmann fraction A+I is resolubilized by resuspending said plasma-derived immunoglobulin fraction under conditions to adjust the conductivity of the suspension to at least 1 mS/cm. This results in a suspension containing resolubilized immunoglobulin which is essentially comprised of IgG, IgM and IgA. While lower conductivities would be sufficient to resolubilize most of the IgG present in the plasma-derived immunoglobulin fraction, a conductivity of at least 1 mS/cm is required to resolubilize a sufficient amount of immunoglobulins IgM and IgA. Typically, the amount of resolubilized immunoglobulin, specifically IgA and IgM, increases with increasing conductivity of the suspension, and the conductivity of the suspension is adjusted to resolubilize as much of the immunoglobulin contained in the plasma-derived starting material as possible. Preferably the plasma-derived immunoglobulin fraction is resuspended under conditions to adjust the conductivity of the suspension to at least 1.5 mS/cm, more preferably to at least 2.0 mS/cm, and most preferably to at least 2.5 mS/cm. The upper limit of conductivity in the suspension is not critical. However, as proteolytic activity tends to increase at very high conductivities, conductivity of the suspension is typically adjusted to a range of from 1.0 mS/cm to 16.0 mS/cm.

Conductivities of at least 1.0 mS/cm described above are sufficient to resolubilize at least 80% by weight, more preferably at least 85% by weight, and most preferably at least 90% by weight of the immunoglobulin contained in the plasma-derived immunoglobulin fractions which are used as the starting material. The proportion of IgM in the suspension obtained under these conditions typically is in the range of from 5% to 11% by weight, preferably at least 6% by weight and more preferably at least 7% by weight, and the proportion of IgA in the resolubilized immunoglobulin is typically in the range of from 10% to 14% by weight, preferably at least 10.5% by weight, and more preferably at least 11% by weight, each based on the total weight of resolubilized immunoglobulin in the suspension. The proportion of IgG in the resolubilized immunoglobulin is typically in the range of from 75% to 85% by weight. Resuspending the plasma derived immunoglobulin fractions at conductivities as described above typically results in a yield of IgM in the suspension which is at least 5 g IgM/kg fraction, preferably at least 7 g IgM/kg fraction, and more preferably at least 9 g IgM/kg fraction, and in a yield of IgA in the suspension which typically is at least 11 g IgA/kg fraction, preferably at least 12 g IgA/kg fraction, and more preferably at least 13 g IgA/kg fraction. The yield of IgG in the suspension is typically at least 90 g IgG/kg fraction and preferably at least 95 g IgG/kg fraction. Typically, the weight ratio of IgM to IgA in the resolubilized immunoglobulin is about 2:3. Weight amounts of immunoglobulins indicated herein may be easily determined according to methods known in the art, for example using nephelometry in accordance with the European Pharmacopoeia 8.0, 2.2.1 (Siemens BN Prospec System).

Typically, resuspending the plasma-derived immunoglobulin fraction under conditions to adjust the conductivity is carried out by resuspending the plasma-derived immunoglobulin fraction using a buffer having a suitable pH and molarity. Typically, the buffer has a pH in the range of from 4.2 to 5.5, preferably of from 4.5 to 5.3, and a molarity in the range of from 0.025 to 0.2 M, preferably of from 0.05 to 0.15 M, and usually of about 0.1 M. While optimum molarities of the buffer to be used may depend on the amount of salts already present in the plasma-derived immunoglobulin fraction to be resuspended, molarities significantly below 0.025 M may result in a reduced resolubilization of IgM and IgA, while molarities significantly above 0.2 M may result in an exceedingly high conductivity and, thus, in a more pronounced resolubilization of proteolytic activities. The type of buffer is not critical as long as there is no adverse effect on the immunoglobulin. Typically, however, resolubilization is carried out using an acetate buffer, in particular a sodium acetate buffer. For resuspension, the weight ratio of buffer to plasma-derived immunoglobulin fraction typically is in the range of from 3+1 to 7+1, preferably of from 4+1 to 6+1, and most preferably from 4.5+1 to 5.5+1.

At the conductivities required in the process of the invention, part of the contaminating protein contained in the starting material remains undissolved and can be separated from the immunoglobulin-containing suspension. The properdin contained in the starting material, however, is found in the resolubilized material. Moreover, while the proportion of resolubilized IgM and IgA in the suspension increases with increasing conductivities, increasing conductivities also increase the amount of properdin found in the resolubilized material, which thus intensifies the task to remove the properdin in the subsequent process steps.

The suspension containing the resolubilized immunoglobulin obtained in step (a) is subjected to a precipitation and, optionally, adsorption step (b), wherein contaminating protein in the suspension is precipitated and adsorbed and can thus be removed from resolubilized immunoglobulin together with other non-resolubilized protein to obtain an impurity-depleted immunoglobulin composition, i.e., an immunoglobulin composition containing IgG, IgM and IgA having a reduced content of contaminating protein. In this step, a major part of contaminating protein is removed except for the properdin which surprisingly stays dissolved with the immunoglobulin.

Typically, precipitation in step (b) comprises treating the suspension obtained in step (a) with a C7- to C9-carboxylic acid, preferably octanoic acid, to inactivate virus and to precipitate contaminating protein (e.g. proteases, viruses etc.). This precipitation step is well known in the art and is described, e.g., in EP 0 447 585 A, WO 2011/131786 and WO 2011/131787. The precipitated protein is removed from the immunoglobulin-containing suspension to obtain the impurity-depleted immunoglobulin composition.

Treatment with the C7- to C9-carboxylic acid, in particular octanoic acid, may be effected by contacting the suspension containing the resolubilized immunoglobulin with the acid, for example by adding the acid to the suspension or by generating the acid in the suspension. The C7- to C9-carboxylic acid is preferably present at a concentration of at least 0.35 g carboxylic acid/g protein and up to a concentration of 0.8 g carboxylic acid/g protein. Higher amounts of acid may be used as well, but typically result in a loss of immunoglobulin yield. More preferably, the acid is present at 0.45 g carboxylic acid/g protein to 0.6 g carboxylic acid/g protein, and most preferably at about 0.5 g carboxylic acid/g protein. The protein concentration before addition of the carboxylic acid is typically of from 20 and 60 g/l, preferably of from 25 to 40 g/l.

According to a preferred embodiment of the invention, treatment of the suspension containing the resolubilized immunoglobulin with, e.g., octanoic acid is carried out by mixing using a vibrating agitator. As described, for example, in WO 2011/131786, the use of a vibrating agitator may result in a higher inactivation and removal of virus particles, especially non-enveloped viruses which are usually not very susceptible to octanoic acid treatment, and provides a more efficient removal of unwanted proteins (including proteases). This results in an intermediate product which is better suited to further downstream processing steps. Any type of commercially available vibrating agitator, suitable for use in the chemical/pharmaceutical industry, may be used. Examples of suitable vibrating agitators are available from Graber+Pfenninger GmbH. In particular, the "Labormodell Typ 1" vibromixer can be used for lab scale experiments, and the "Industriemixer Typ 4" can be used for production scale preparations. The vibrating mixers can be used according to manufacturer's instructions, and in particular at settings which are described by the manufacturers as suitable for mixing solutions containing proteins. For example, the vibrating mixers can usually be operated at less than 100 Hz with an amplitude less than 10 mm, e.g. the vibration mixing using the "Labormodell Typ 1" at lab scale was carried out by the present inventors at 50 Hz, when 230 V power supply is used. The vibration amplitude of the mixing process may preferably be varied between 0 and 3 mm. Stirrer plates with a diameter between 23 mm and 65 mm may be used for lab scale experiments, and for production scale a stirrer plate diameter of 395 mm may be used (hole diameters of 13.5 mm and 16 mm).

The pH value of the suspension in step (b) during mixing is preferably adjusted to a range of from 4.3 to 5.5, and more preferably of from 4.5 to 5.3. Mixing can be carried out using sodium acetate buffer, for example, an about 0.1 M sodium acetate buffer. The temperature at which mixing in step (b) is conducted is preferably in the range of from 16° C. and 35° C., and more preferably of from 18 and 30° C. The mixing time using the vibrating agitator is not particularly limited but is preferably at least 10 minutes and not more than 3 hours, and more preferably in the range of from 40 to 120 minutes. Incubation times of less than 30 minutes can reduce the level of virus inactivation.

According to a further embodiment of the invention, C7- to C9-carboxylic acid treatment in step (b) may include treating the resolubilized immunoglobulin suspension with an adsorbent such as tri-calcium phosphate to precipitate and adsorb protein. Preferably, adsorbents such as tri-calcium phosphate are added at a concentration of 0.01 to 0.02 kg/kg of the suspension. The tri-calcium phosphate can be added simultaneously, separately or sequentially to the carboxylic acid. In a preferred embodiment the tri-calcium phosphate is added at least 20 minutes after starting the treatment with the carboxylic acid.

Precipitated contaminating protein is removed from the suspension to obtain an impurity-depleted immunoglobulin composition having a reduced content of contaminating protein. This removal step is not particularly limited but can be performed by any suitable method known in the art. Preferably, the removal step is performed using filtration, optionally followed by an ultrafiltration and/or diafiltration step to remove carboxylic acid such as octanoic acid used for the precipitation. The impurity-depleted immunoglobulin composition obtained in step (b) preferably comprises, based on a total amount of 40 g/l of protein in the composition, thrombogenic activity (TGA) <3 mU/ml; prekallikrein activator <10%, more preferably <5% of normal human plasma; proteolytic activity <20 U/l; and $\alpha_2$-macroglobulin <0.2 g/l. More specifically, thrombogenic activity (TGA) <1.5 mU/ml; prekallikrein activator <2.5% of normal human plasma; proteolytic activity <11 U/l; and $\alpha_2$-macroglobulin <0.1 g/l can be achieved in step (b). The properdin content in this intermediate compositions is typically more than 75 µg/mg protein.

Following removal of contaminating protein, step (b) may further include a mild acid treatment for further virus inactivation. For mild acid treatment, the immunoglobulin composition obtained after protein removal is incubated at a pH in the range of from 3.8 to 4.5, and preferably of from 3.9 to 4.1, to form an incubated solution. The mild acid conditions can be created by adding a suitable acid to the immunoglobulin composition. For example, the pH can be adjusted to the desired value by the addition of 0.2 M HCl. This incubation step is preferably carried out at a temperature in the range of from 35 to 40° C. The incubation time is preferably at least 2 hours and not longer than 24 hours, and more preferably at least 9 hours but not longer than 16 hours.

Following treatment with carboxylic acid and, optionally, adsorbent, the impurity depleted immunoglobulin composition typically has an IgG content in the range of from about 85 to 94% by weight, an IgA content in the range of from about 3 to 9% by weight, and an IgM content in the range of from about 3 to 9% by weight, based on the total amount of immunoglobulin in the impurity depleted immunoglobulin composition.

In step (c) the impurity-depleted immunoglobulin composition of step (b), preferably following mild acid treatment, is subjected to ion exchange chromatography using an anion exchange resin disposed in a column. Anion exchange chromatography is carried out under conditions of pH and conductivity adjusted to substantially bind IgM and IgA and, optionally, IgG to the anion exchange resin. The term "substantially" as used herein means that at least 90% by weight, preferably at least 95% by weight, and most preferably at least 98% by weight of each individual immunoglobulin IgM, IgA and/or IgG is bound to the resin, based on the amount of each immunoglobulin subjected to anion exchange chromatography. Depending on whether the solution conditions of anion exchange chromatography are adjusted to substantially bind IgG or not, IgG-enriched immunoglobulin compositions may be obtained in the flow-through fraction and/or following elution of IgG from the anion exchange resin under conditions of pH and conductivity where IgM and IgA remain bound on the anion exchange resin. Following recovery of IgG, immunoglobulin compositions enriched in IgM and/or IgA may optionally be obtained by eluting IgM and/or IgA from the anion exchange resin. Irrespective of whether IgG is obtained in the flow-through or following elution, however, properdin is always found together with the IgG in the IgG-enriched immunoglobulin fraction.

According to a preferred embodiment of the invention, the impurity-depleted immunoglobulin composition obtained in step (b) is contacted with the anion exchange resin under conditions of pH and conductivity where IgM and IgA are substantially bound to the anion exchange resin and IgG is obtained as an IgG-enriched immunoglobulin composition in the flow through fraction. Typically, flow-through conditions are achieved by subjecting the impurity-depleted immunoglobulin composition to anion exchange chromatography under solution conditions of a pH which is adjusted to a range of from 6.7 to 7.5, preferably of from 6.9 to 7.3, and most preferably at a pH of about 7.1, and a conductivity which is adjusted to a range of from 4 to 7.5 mS/cm, and preferably of from 5.5 to 7 mS/cm. Conductivities in the solutions used for chromatography are typically adjusted by adjusting the salt concentration, for example with NaCl. If anion exchange chromatography is carried out at pH values of less than 6.7 and/or at conductivities of more than 7.5 mS/cm, the IgG content in the IgG-enriched flow-through fraction will increase, but the flow-through may contain an undesirably high IgA content. Therefore, under these conditions minor amounts of IgG will remain bound to the anion exchange resin but the major part of the IgG will be found in the flow-through. The anion exchange resin that contains bound IgM, IgA and residual IgG immunoglobulins may be washed with a washing buffer such as a Tris/HCl buffer, and the washing fraction may be combined with the IgG-containing flow-through.

According to a further embodiment of the invention, the impurity-depleted immunoglobulin composition may be contacted with the anion exchange resin under solution conditions of pH and conductivity where all immunoglobulins, i.e., IgG, IgM and IgA, are substantially bound to the resin. Typically, these conditions are achieved at pH values above those used for binding of IgM and IgA, in particular at pH values of 8 or more, and at low conductivities, in particular at conductivities of 2 mS/cm or less. Bound IgG is then eluted to obtain an IgG-enriched immunoglobulin composition using elution buffers under the conditions described above for the flow-through mode under which minor amounts of IgG will remain bound to the anion exchange resin.

Following recovery of IgG to obtain IgG-enriched immunoglobulin compositions, immunoglobulin compositions enriched in IgM and/or IgA may be obtained by eluting IgM and/or IgA bound to the anion exchange resin from the resin together with residual IgG. Immunoglobulins IgM and IgA may be eluted independently of each other or altogether. Preferably, however, IgM and IgA will be eluted together and with the residual IgG bound to the anion exchange resin to obtain an immunoglobulin composition that is enriched in IgM and IgA. Following elution of IgM, IgA and residual IgG from the resin, the IgG content in the resulting immunoglobulin fraction is sufficiently high to have a stabilizing effect on the IgM molecules in the IgM- and IgA-enriched immunoglobulin composition. Typically, immunoglobulin compositions enriched in IgM and IgA comprise IgM in a range of from 10 to 35% by weight, IgA in a range of from 10 to 35% by weight, and IgG in a range of from 40 to 75% by weight, based on the total amount of immunoglobulin in the eluted fraction. Preferably, the IgM- and IgA-enriched immunoglobulin compositions comprise IgM in a range of from 15 to 30% by weight, most preferably at least 18% by weight, IgA in a range of from 15 to 30% by weight, and IgG in a range of from 45 to 70% by weight, based on the total amount of immunoglobulin in the eluted fraction. In these IgM- and IgA-enriched immunoglobulin compositions, the IgG typically has an IgG subclass distribution, on a molecular basis, which is enriched in IgG-4 to more than 10%, preferably more than 12%, and most preferably more than 15%, in relation to total IgG content. This results in a lower antibody dependent cell-mediated cytotoxicity (ADCC) when administered to a patient and, thus, improves the quality of the final pharmaceutical preparations.

Typically, elution of IgM, IgA and residual IgG is carried out under conditions comprising a conductivity in the elution buffer which is adjusted to elute all bound immunoglobulins in one or more subfractions, typically by increasing the salt concentration, for example with NaCl. Preferably, elution is carried out at a conductivity adjusted to at least 20 mS/cm, more preferably at least 25 mS/cm, and most preferably at least 28 mS/cm. Lower conductivities are less desirable as this may result in an incomplete elution of IgM from the anion exchange resin and, as a consequence, in a composition having a reduced IgM content. The upper limit of the conductivity usually is not critical for IgM elution as long as it does not result in an undesired elution of bound impurities. Therefore, conductivity should be sufficiently low and preferably below 40 mS/cm to avoid elution of non-immunoglobulin impurities firmly bound to the resin into the IgM/IgA/IgG eluate. Typically, elution is carried out at a pH adjusted within a range of from 6.5 to 7.5.

The IgM- and IgA-enriched immunoglobulin preparations obtained above may have a degree of impurities, based on a total amount of 50 g/l of immunoglobulin preparation of: thrombogenic activity (TGA) <3 mU/ml; prekallikrein activator <10%, preferably <5% of normal human plasma; factor XIa <0.2 mU/ml; and ceruloplasmin <0.1 g/l. Impurities may even be as low as: thrombogenic activity (TGA) 1.5 mU/ml; prekallikrein activator <2.5% of normal human plasma; and ceruloplasmin <0.02 g/l.

The type of anion exchange resin used in step (c) is not particularly limited and includes any conventional anion exchange resin. Suitable anion exchange resins include, for example, macroporous anion exchange resins and anion exchange resins having tentacle structures. Macroporous anion exchange resins, in particular those having no tentacle structure, are preferred as they show higher pressure stability and thus allow higher flow rates. However, anion exchange resins having tentacle structures such as those available under the trade name Fractogel® can be used as well.

The pore size of the macroporous anion exchange resins should be large enough to adsorb IgM and IgA molecules from the immunoglobulin compositions in the pores. Macroporous anion exchange resins used in the process of the invention typically have nominal pore sizes of at least 50 nm, for example in a range of from 50 to 400 nm. The upper pore size is not particularly critical and is limited only by pressure stability and/or surface area of the resin. Pore size of macroporous anion exchange resins can be determined in a conventional manner by mercury porosimetry in accordance, for example, with Ph. Eur. 7.0, 2011, 2.9.32. The ionic functional group of the anion exchange resins useful in the invention is not critical. Useful anion exchange resins typically may contain primary, secondary, tertiary or quaternary ammonium groups such as trimethylaminoethyl (TMAE) groups, or quaternized polyethyleneimine. Strong anion exchange resins are preferred. Macroporous anion exchange resins useful in the process of the invention are commercially available, for example under the trade names POROS® 50 HQ (Applied Biosystems), Macro-Prep® HQ (Bio-Rad Laboratories, Inc.), Fractogel® EMD TMAE (Merck Millipore), Eshmuno® Q (Merck Millipore) and CIM® QA (Bio Separations). Anion exchange resins such as POROS® 50 HQ are preferred.

Typically, the amount of immunoglobulin loaded onto the anion exchange resin is within a range of from 30 to 50 g/l of resin, preferably of from 35 to 45 g/l of resin. Lower amounts are less economical while higher amounts (e.g., more than 50 g/l of resin) may result in an increased amount of IgA in the flow-through.

Preferably, ion exchange chromatography with macroporous anion exchange resins is carried out at linear flow rates of at least 200 cm/h, more preferably at least 450 cm/h, and most preferably at least 600 cm/h. Under these conditions, bed heights of the column advantageously are 20-30 cm. Thus, use of macroporous anion exchange resins allows significant shortening of processing time for large industrial batches such as batches of more than 10 kg of protein or even more than 30 kg of protein per batch. Shortening of processing times by reducing cycle number otherwise requires much larger columns and much more chromatography resin, which makes the process technically more complicated and expensive. It has been found that immunoglobulin solutions can be stably processed under these conditions of high flow rates and high pressure, although the highly susceptible IgM molecule otherwise tends to be unstable under a variety of conditions.

The IgG-enriched immunoglobulin compositions obtained in step (c) in the flow-through fraction and/or following elution from the anion exchange resin typically have an IgG content of at least 95% by weight, preferably at least 98% by weight, and more preferably at least 99%, 99.5%, 99.7% or even 99.9% by weight, based on the total weight of immunoglobulin in the IgG-enriched immunoglobulin composition. These compositions, however, still have an ACA which is too high to meet the acceptance limit according to the European Pharmacopoeia. As discussed above, the high ACA was found to be due to the presence of properdin which is already present in high amounts in Cohn fraction I/II/III and Kistler-Nitschmann fraction A+I and is removed neither in purification step (b) nor by anion exchange chromatography in step (c).

It has now been found that the undesirably high ACA can be reduced in step (d) by subjecting the IgG-enriched immunoglobulin composition to treatment with a cation exchange material under solution conditions of pH and conductivity where properdin is bound to the cation exchange material, and recovering IgG from the cation exchange material in the flow-through fraction and/or by eluting IgG from the cation exchange material under conditions where properdin remains bound to the cation exchange material to thereby obtain an IgG-enriched immunoglobulin composition having a reduced properdin content.

Treatment of the IgG-enriched immunoglobulin composition with the cation exchange material may be carried out in batch mode or in continuous mode, wherein the cation exchange material may be disposed in a vessel or a chromatography column or may be in the form of a cationic membrane adsorber.

Preferably, treatment of the IgG-enriched immunoglobulin composition in step (d) is carried out by subjecting the IgG-enriched immunoglobulin composition to cation exchange chromatography under conditions where properdin is bound to the cation exchange material and IgG is essentially prevented from binding to said cation exchange material. IgG then is recovered from the cation exchange material as unbound immunoglobulin in the flow through fraction. For economic reasons, conditions for contacting the IgG-enriched immunoglobulin composition with the cation exchange material are typically adjusted to prevent IgG from binding to the cation exchange material to an extent of more than 1% by weight, based on the weight of total IgG contained in the IgG-enriched composition subjected to cation exchange chromatography. Typically, cation exchange chromatography is carried out under conditions adjusted, independently, to a pH in the range of from 5.0 to 6.0, preferably of from 5.2 to 5.8, and most preferably of from 5.4 to 5.6, and a conductivity in the range of from 16 to 30 mS/cm, preferably of from 20 to 28 mS/cm, and most preferably of from 22 to 26 mS/cm.

According to a further embodiment of the invention, treatment of the IgG-enriched immunoglobulin composition in step (d) is carried out by contacting the IgG-enriched immunoglobulin composition with a cationic membrane adsorber under conditions where properdin is bound to the cationic membrane adsorber and IgG is essentially prevented from binding to said cationic membrane adsorber. IgG is then recovered as unbound immunoglobulin from the cationic membrane adsorber in the flow-through fraction. Conditions for contacting the IgG-enriched immunoglobulin composition with the cationic membrane adsorber correspond to those used for cation exchange chromatography.

Alternatively, treatment of the IgG-enriched immunoglobulin composition may comprise subjecting the IgG-enriched immunoglobulin composition to cation exchange chromatography, or contacting with a cationic exchange membrane, under conditions of low conductivity where both properdin and IgG are bound to the cation exchange material. The bound IgG is then recovered from the cation exchange material by eluting the IgG from the resin under conditions where properdin remains bound to the cationic exchange material. Typically, IgG is eluted from the cation exchange material using an elution buffer adjusted, independently, to a pH and a conductivity which are the same as used above for preventing IgG from binding to the cation exchange resin, i.e., a pH value in the range of from 5.0 to 6.0, preferably of from 5.2 to 5.8, and most preferably of from 5.4 to 5.6, and a conductivity in the range of from 16 to 30 mS/cm, preferably of from 20 to 28 mS/cm, and most preferably of from 22 to 26 mS/cm.

The cation exchange material used for cation exchange chromatography or with cationic membrane adsorbers is not particularly limited and includes any conventional cation exchange resins suitable for IgG chromatography such as weak and strong cation exchange resins containing carboxylic acid groups or sulfonic acid groups, e.g., sulfopropyl groups, and having pore sizes allowing IgG to diffuse into the pores. Suitable cationic exchange resins are commercially available, for example under the trade name POROS® HS, such as POROS® HS 50, Fractogel® EMD $SO_3^-$, and Eshmuno® CPX. The cation exchange material may be disposed in a vessel or a chromatography column. Cationic membrane adsorbers are commercially available, for example, under the trade name Sartobind S.

Protein load for the cation exchange material typically is up to 5 g of protein/g cation exchange material, and preferably is in a range of from 0.01 g to 5 g protein/g cation exchange material, for example of from 0.1 g to 5 g protein/g cation exchange material. Flow rates for cation exchange chromatography usually range of from 200 to 800 cm/h and for cationic membrane adsorbers may be up to 5000 cm/h.

Treatment of properdin-containing IgG compositions with cation exchange materials as described above in step (d) of the process of the invention for IgG-enriched immunoglobulin compositions obtained after anion exchange chromatography can also be used to reduce the properdin content in properdin-containing IgG compositions in general.

Therefore, the present invention is further directed to a process for reducing the properdin content in a properdin-containing IgG composition, said process comprising subjecting said properdin-containing IgG composition to treatment with a cation exchange material under conditions of pH and conductivity where properdin is bound to said cation exchange material to obtain an IgG composition having a reduced properdin content.

The properdin-containing IgG composition subjected to treatment with a cation exchange material may be an IgG-enriched immunoglobulin composition which preferably has an IgG content of at least 95% by weight, preferably at least 98% by weight, and most preferably at least 99% by weight, based on the total weight of immunoglobulin in the properdin-containing IgG composition.

The IgG preparation obtained after treatment with the cation exchange material and recovery is polyclonal and has an IgG content which is substantially the same as after anion exchange chromatography but with a reduced properdin content. Typically the IgG content of the IgG-enriched immunoglobulin compositions obtained after treatment with the cation exchange material is at least 95% by weight, preferably at least 98% by weight, and more preferably at least 99%, 99.5%, 99.7% or even 99.9% by weight, based on the total weight of immunoglobulin in the IgG-enriched immunoglobulin composition. Preferably, the IgG preparation, on a molecular basis, contains at least 1.0%, preferably at least 1.4%, and more preferably at least 2.0% of IgG-4, based on total IgG content, which is sufficiently similar to the natural distribution. IgG subclass distribution may be determined according to methods known in the art, for example using nephelometry in accordance with Ph. Eur. 7.0, 2011; 2.7.1 (Siemens BN Prospec System).

The recovered IgG that is obtained, for example, following cation exchange chromatography or treatment with a cationic membrane adsorber may be subjected to further conventional downstream processing for virus inactivation and concentration. Specifically, the recovered IgG may be subjected to nanofiltration to remove potentially present virus using a nanofilter having a pore size of about 20 nm. The resulting solution may be further concentrated by ultrafiltration and/or diafiltration.

Similarly, the IgM- and IgA-enriched immunoglobulin compositions obtained after anion exchange chromatography, optionally following further concentration, for example by ultrafiltration, may be subjected to subsequent treatment for virus inactivation to obtain a virus inactivated preparation. Virus inactivation may comprise nanofiltration and/or UVC irradiation.

Irradiation may be carried out by methods known in the art and described, for example in WO 2011/131786 and WO 2011/131787. Specifically, eluates may be treated with UVC light to form a UVC irradiated solution using devices which are commercially available, such as the UVivatec® device (Bayer Technology Services). It is preferred that the incubated solution is treated at 254±10 nm between 200 and 500 $J/m^2$, more particularly between 200 and 300 $J/m^2$, in order to further inactivate viruses which are potentially present. UVC treatment under gentle conditions is also possible with the water-clear filtrate which is obtained after the octanoic acid treatment. More opalescent or opaque solutions, however, may necessitate longer irradiation times with potentially damaging effects on the immunoglobulins. Typically, UVC irradiation is only carried out after anion exchange chromatography has been completed.

The immunoglobulin solution being processed may also be filtered through a nanofilter for virus inactivation. Filters of 75±5 nm to 35±5 nm pore size, or filters having a nominal pore size of 75 to 35 nm (for example Pall Ultipor DV50), can be used at various stages during the process (a nominal pore size of e.g. 50 nm means a retention rate of ≥4 log 10 for virus with size of 50 nm or larger). In a preferred embodiment the immunoglobulin solution obtained before UVC irradiation is subjected to nanofiltration, preferably through a filter having a 40 to 50 nm pore size. It is preferred that this step should be carried out under sterile conditions.

Preferably the process of the present invention does not comprise one or more of chemical or enzymatic modification of the immunoglobulin in the preparation or heat treatment of the immunoglobulin (e.g. treatment of the immunoglobulin at a temperature of 42° C. or more for 10 minutes or more). More particularly, the process of the present invention does not include a step of contacting the antibodies with β-propiolactone and/or pepsin.

The process of the present invention allows for the parallel manufacture of IgG-enriched and IgM- and/or IgA-enriched immunoglobulin compositions with high purity and with excellent yield. The process starts from plasma fractions containing essentially all immunoglobulin present in normal blood plasma and without the need for a separate precipitation of IgG-rich fractions such as Cohn fraction II.

Moreover, the process of the present invention allows the preparation of IgG-enriched pharmaceutical immunoglobulin compositions having a low ACA even from blood plasma pooled from 500 donors or more. Blood plasma pooled form hundreds of donors is characterized by a high antibody diversity and usually can be expected to have a high ACA. The IgG-enriched immunoglobulin composition obtainable by the process of the invention and comprising IgG from more than 500 donors, however, has extremely low contents of properdin and of IgG polymers and, in addition low residual thrombogenic activity (TGA), Factor XIa (FXIa) and Factor XI (FXI). This results in an ACA of <1 CH50/mg protein as required by the European Pharmacopoeia 8. Experimental data show that IgG-enriched immunoglobulin compositions obtained by the process of the invention, thus, have a unique combination of properties which is not found in any of the commercial pharmaceutical IgG compositions which are presently available on the market.

The IgG-enriched immunoglobulin composition obtained after treatment with a cation exchange material and virus inactivation may be directly formulated into pharmaceutical immunoglobulin compositions and/or filled into a container under sterile conditions, for example a vial or an ampoule. The present invention, therefore is further directed to an IgG-enriched pharmaceutical immunoglobulin composition obtained from blood plasma of 500 donors or more, wherein said composition has:
(i) an IgG content of at least 45 g/l of the composition;
(ii) an IgG content of at least 95% by weight, based on the total weight of immunoglobulin in the composition;
(iii) a properdin content of not more than 0.01 µg/mg of total immunoglobulin in the composition, and
(iv) a content of IgG polymers of not more than 0.05%, based on the total amount of IgG in the composition.

The IgG-enriched pharmaceutical immunoglobulin compositions are polyclonal and are meant to be immunoglobulin compositions pharmaceutically acceptable for a human subject and suitable for intravenous or intramuscular administration by injection.

Preferably, the IgG-enriched pharmaceutical immunoglobulin composition of the invention has an IgG content in the range of from 45 to 225 g/l (about 5% to about 20%), for example in a range of from 45 to 55 g/l for an about 5% IgG composition, in the range of from 95 to 105 g/l for an about 10% IgG composition, or in a range of from 160 to 210 g/l for a subcutaneous IgG composition.

Preferably, the IgG-enriched pharmaceutical immunoglobulin composition of the invention has an IgG content of at least 98% by weight, more preferably at least 99% by weight, and more preferably at least 99%, 99.5%, 99.7% or even 99.9% by weight, based on the total weight of immunoglobulin in the IgG-enriched pharmaceutical immunoglobulin composition.

Preferably, the IgG preparation, on a molecular basis, contains at least 1.0%, preferably at least 1.4%, and more preferably at least 2.0% of IgG-4, based on total IgG content.

Preferably, the IgG-enriched pharmaceutical immunoglobulin composition of the invention has a properdin content of not more than 0.005 µg/mg immunoglobulin in the composition.

Preferably, the IgG-enriched pharmaceutical immunoglobulin composition of the invention has a content of IgG polymers of not more than 0.01%, based on the total amount of IgG in the composition. IgG polymers are defined as higher aggregates of IgG molecules which are not IgG monomers, IgG dimers or IgG fragments. The total amount of IgG in the composition is the sum of IgG monomers, dimers, polymers and any fragments thereof. The proportion of IgG monomers, dimers, polymers and fragments thereof is determined by HPSEC as peak area in percent of the total area of the chromatogram in accordance with the European Pharmacopoeia 8.0 (2.2.30—Molecular size distribution of "Human normal immunoglobulin for intravenous administration").

Typically, the content of IgG polymers in the IgG-enriched pharmaceutical immunoglobulin composition does not change following long-term storage at a temperature of 5° C. and is preferably not more than 0.05%, more preferably not more than 0.01% after storage over a period of 15 months, preferably of 21 months.

Typically, the content of IgG polymers in the IgG-enriched pharmaceutical immunoglobulin composition after long-term storage at a temperature of 25° C. over a period of 15 months, preferably over a period of 21 months, is not more than 1.0%, preferably not more than 0.75%, determined by HPSEC as described above.

The IgG-enriched pharmaceutical immunoglobulin composition of the invention may contain stabilizers such as glycine and proline but preferably is free of carbohydrates such as sugars and sugar alcohols, for example sorbitol, mannitol, glucose and trehalose. Preferably, the composition is formulated with a stabilizer such as glycine or proline, and in particular the composition may be formulated in a glycine- or proline-containing buffer at a pH in the range of from 4 to 5.5, preferably of from 4.2 to 4.8, and most preferably at about pH 4.6.

Preferably, the IgG-enriched pharmaceutical composition has less than 2.0 mU/ml of Factor XIa.

Preferably, the IgG-enriched pharmaceutical composition contains less than 1% of norm (Standard Human Plasma; Siemens Healthcare) of Factor XI.

Preferably, thrombogenic activity in the IgG-enriched pharmaceutical composition is less than 1.5 mU/ml.

The IgG-enriched pharmaceutical immunoglobulin composition of the invention preferably is not pasteurized.

The IgG- and IgM/IgA-enriched immunoglobulin compositions obtainable by the process of the invention have a low ACA and can be used as intravenous immunoglobulin compositions which meet the requirements of European Pharmacopoeia. In particular, the immunoglobulin compositions have the advantage of: (i) being chemically unmodified; (ii) having low proteolytic activity; (iii) having low anticomplementary activity; and (iv) containing high levels of native and biologically active IgG, IgM and/or IgA.

EXAMPLES

Determination of Immunoglobulin Content

The immunoglobulin content was determined by capillary zone electrophoresis (CZE) according to the European Pharmacopoeia 8.0 (2.2.47—Capillary Electrophoresis). Immunoglobulin fractions were separated at pH 10 in capillaries according to their charge:mass ratio on the basis of their run time, characterized and quantified photometrically at 200 nm. A capillary electrophoresis system with UV detector (P/ACE MDQ capillary electrophoresis system, Beckman Coulter) was used for the procedure. The samples were diluted with electrophoresis buffer to a protein concentration of 2.5 g/l (borate buffer, pH 10; 14.3 g disodium tetraborate decahydrate dissolved in 1000 ml Aqua purificata and adjusted with 1 M NaOH). The mixture is used for electrophoresis without any further preparation. The electrophoresis procedure is performed according to the instrument manufacturer's instructions.

Determination of Molecular Size Distribution

The molecular size distribution of IgG immunoglobulins was determined by High Pressure Size Exclusion Chromatography (HPSEC) as peak area in percent of the total area of the chromatogram according to the European Pharmacopoeia 8.0 (2.2.30—Molecular size distribution of "Human normal immunoglobulin for intravenous administration"). On passing protein mixtures through hydrophilic porous gels, the molecules appear in different distribution zones depending on molecular size and pore size distribution. The largest proteins/particles migrate through the gel most rapidly while small protein molecules and low molecular weight substances migrate most slowly.

A Tosoh TSK-G 3000 SW was used for separation, and a protein mass of 100 μg was injected. The separated fractions were detected and quantified at the column outlet by photometry at 280 nm. The chromatography was performed according to the equipment manufacturer's operating instructions. A Bio-Rad gel filtration standard was used as a control. An immunoglobulin preparation was used as SST-sample. The peaks are assigned to the fractions polymer, dimer, monomer and fragments, using an automated method for peak integration.

Determination of Properdin Concentration

A ready-to-use solid phase human properdin ELISA kit (Hycult Biotech) was used for the in vitro quantitative determination of human Properdin in IgG preparations in accordance with the manufacturer's instructions. Briefly, samples and standards are incubated in microtiter wells coated with antibodies recognizing human properdin. Biotinylated tracer antibody will bind to the captured human properdin. Streptavidin-peroxidase conjugate will bind to the biotinylated tracer antibody. Streptavidin-peroxidase conjugate will react with the substrate, tetramethylbenzidine (TMB). The enzyme reaction is stopped by the addition of oxalic acid. The absorbance at 450 nm is measured with a spectrophotometer. A standard curve is obtained by plotting the absorbance (linear) versus the corresponding concentrations of the human properdin standards (log). The human properdin concentration of samples, which are run concurrently with the standards, is determined from the standard curve.

Determination of Anticomplementary Activity (ACA)

Tests for ACA of immunoglobulin were performed as described in the European Pharmacopoeia 8.0 (2.6.17—Test for Anticomplementary Activity of immunoglobulin).

In brief, a defined amount of test material (10 mg of immunoglobulin) is incubated with a defined amount of guinea pig complement (20 $CH_{50}$). The remaining complement is titrated and incubated with red sheep blood cells that are sensitized with hemolysin. Optimally sensitized sheep red blood cells consist of sheep erythrocytes loaded with antibodies against sheep erythrocytes (hemolysin). The degree of cell lysis is determined by photometry at 541 nm. ACA is expressed as the percentage consumption of complement relative to a complement control considered as 100 percent. The hemolytic unit of complement activity ($CH_{50}$) is defined as the amount of complement that, in the given reaction conditions, will produce lysis of half of the sensitized sheep red blood cells in the test. The acceptance limit for ACA in the European Pharmacopoeia is defined as such that the consumption of complement is not greater than 50 percent and 1 $CH_{50}$ per milligram of immunoglobulin.

Thrombogenic Activity (TGA)

A fluorogenic microplate assay (Technoclone) was used to determine thrombogenic activity (TGA). Technothrombin® TGA RC High was used as reagent, Technothrombin® TGA SUB as fluorogenic substrate, and a Factor XI deficient plasma. Calibration was done with the International Standard for FXIa, 13/100 (NIBSC).

Factor XI (FXI)

A commercially available standard coagulation assay (Siemens Healthcare Diagnostics) was used to determine Factor XI (FXI). FXI depleted plasma, Actin FSL as activator and a $CaCl_2$ solution were used in this assay. Calibration was done with Standard Human Plasma (Siemens Healthcare). Additional calibration points in the lower calibration range were included to improve assay sensitivity.

Factor XIa (FXIa)

A commercially available chromogenic assay (Hyphen Biomed) was used to determine Factor XIa employing the standard conditions of the test kit.

Example 1

Example 1a

Preparation of an IgM-Enriched Immunoglobulin Composition

Human blood plasma for fractionation (2000 l) from more than 500 donors was used as starting material. The plasma was transferred to the pooling area and pooled.

A cryoprecipitation step was performed in order to separate coagulation factors such as Factor VIII, von Willebrand Factor, and Fibrinogen. In order to obtain the cryoprecipitate, the temperature of the plasma was adjusted under gentle stirring so that the temperature range was kept at 2±2° C. Under these conditions the cryoprecipitate remains undissolved in the thawed plasma. The cryoprecipitate was separated from the plasma by a continuously operating centrifuge such as a Westfalia separator.

From the supernatant of the cryoprecipitation step the Cohn fraction I/II/III was precipitated by ethanol precipitation as follows:

The temperature of the centrifugation supernatant remaining after separation of the cryoprecipitate was adjusted to 2±2° C. The pH-value of the protein solution was adjusted to pH 5.9. Subsequently, the temperature was lowered to −5° C. and ethanol was added to a final concentration of 20% by volume. Under constant slow stirring in a stainless steel vessel, Cohn Fraction I/II/III was precipitated. The Cohn Fraction I/II/III precipitate was separated from the supernatant by filtration with depth filter sheets under addition of filter aid such as Perlite or Diatomaceous Earth, using a filter press. The Cohn fraction I/II/III was recovered from the filter sheets. This Cohn fraction I/II/III precipitate comprised all immunoglobulins (IgG, IgA, IgM) in approximately the following percentages: 75% IgG, 13% IgM and 12% IgA.

90 kg of the obtained Cohn fraction I/II/III precipitate were resuspended in 450 kg of 0.1 M sodium acetate puffer pH 4.8 and mixed for 60 minutes at 22° C. The pH of the suspension was adjusted to 4.8 with acetic acid.

In the following a treatment with octanoic acid was performed. The solution was treated by addition of 7.7 kg octanoic acid at room temperature. The octanoic acid was added slowly and the protein solution was further mixed for 60 minutes, using a vibrating mixer (Vibromixer®, Size 4, Graber+Pfenniger GmbH, Vibromixer adjusted to level 2-3).

A calcium phosphate treatment was performed in order to complete the octanoic acid reaction as follows:

Approximately 1.1 kg $Ca_3(PO_4)_2$ were added and the protein solution was further mixed for more than 15 minutes and filtered over depth filter sheets. The filtrate was further processed. The obtained protein solution was subjected to ultrafiltration to a protein concentration of about 50 g/l. The protein solution was diafiltered against 0.02 M sodium acetate buffer pH 4.5 and afterwards adjusted to a protein concentration of about 40 g/l.

The protein solution was treated at pH 4.0 in order to inactivate viruses as follows: The pH was adjusted to pH 4.0 using 0.2 M HCl, and the resulting solution was incubated for 8 hours at 37° C. The resulting protein solution contains immunoglobulins with the following distribution: 90% IgG, 5% IgA, and 5% IgM.

The obtained protein solution was further processed by anionic exchange chromatography using a macroporous anion exchange resin in order to remove accompanying proteins and to obtain an IgG- and IgM-enriched immunoglobulin compositions.

Per kilogram of the intermediate protein solution 0.00121 kg of tris(hydroxymethyl)aminomethane (Tris) were added and dissolved while stirring and the conductivity was adjusted to 6 mS/cm with solid NaCl. The protein solution was adjusted to pH 7.1 by adding 1 M NaOH. A macroporous anion exchange resin (POROS® 50 HQ anion exchange resin, Life Technologies, bed height of the column: 25 cm) was equilibrated with a 10 mM Tris buffer solution (pH 7.1, 50 mM NaCl, at a linear flow rate of 800 cm/h). The protein solution was loaded on the anion exchange resin with 40 g protein per liter of resin. The column was washed with the equilibration buffer (10 mM Tris, 50 mM NaCl, pH 7.1, at 800 cm/h).

An IgG-enriched immunoglobulin composition was obtained in the flow-through fraction and was further processed as described in Example 3 below.

An IgM-enriched fraction was eluted by increasing the conductivity as follows: 10 mM Tris buffer solution with 300 mM NaCl at pH 7.1 is used at 800 cm/h to elute the IgM-enriched fraction. The eluted fraction contained 58% IgG, 22% IgA and 20% IgM.

The protein solution was filtered through a Pall, Ultipor VF DV50 filter as a virus removal step. The filtrate was further processed by UVC light treatment at 254 nm, using a flow-through UVivatech process device (Bayer Technology Services/Sartorius) at a UVC dose of 225 J/m$^2$ for further virus inactivation. The flow velocity through the UVC reactor was calculated using the manufacturer's instructions. The irradiated protein solution was concentrated to a protein concentration of 50 g/l by ultrafiltration (and was subjected to diafiltration (using 0.3 M glycine buffer pH 4.5). The final product was filtered through a 0.2 µm filter and was stored at 2 to 8° C.

The obtained immunoglobulin composition had an IgM content of 22% by weight, an IgA content of 22% by weight and an IgG content of 56% by weight, based on the total immunoglobulin content, at an immunoglobulin concentration of 50 mg/ml. The ACA was 0.34 CH50/mg.

Example 1b

Processing of Larger Amounts

In order to process larger amounts of protein, multiple purification cycles on the macroporous anion exchange resin were conducted. For this purpose, cleaning steps were implemented into the chromatography cycle. Specifically, following elution of the IgM-enriched fraction from the IgG-, IgA and IgM-containing intermediate protein solution obtained as described in Example 1a, the column was stripped with 1 M NaCl solution to elute residual bound proteins. The column was further regenerated with 3 column volumes of 1 M NaOH, and a further cycle was started by the equilibration phase using equilibration buffer. In total, 12 purification cycles at a linear flow rate of 800 cm/h were conducted without loss of any purification performance.

Example 2

Preparation of an IgM-Enriched Immunoglobulin Composition Using a Tentacle Resin The initial processing including the step of the pH 4 treatment was done as described in Example 1a.

The obtained protein solution was further processed by anionic exchange chromatography using a tentacle anion exchange resin in order to remove accompanying proteins and to obtain a solution comprising an increased percentage of IgM relative to the other immunoglobulins, as follows:

The intermediate (protein concentration: 41 g/l) was adjusted with Tris buffer (final concentration: 10 mM) to a pH of 7.1. The conductivity of the protein solution was adjusted to 6 mS/cm (at 20° C.) using NaCl.

The chromatography column (Fractogel® TMAE, bed height: 39.5 cm, column volume: 80 ml) was equilibrated with 10 mM Tris buffer pH 7.1/50 mM NaCl at a linear flow rate of 150 cm/h, and the protein solution was pumped onto the chromatography column until a loading of 40 mg per ml resin was reached. The loaded column was washed with 10 mM Tris buffer pH 7.1/50 mM NaCl and the flow-through fraction was collected. The linear flow rate of 150 cm/h was kept during the experiment. The chromatography was monitored using a UV-sensor. The bound fraction was eluted by 10 mM Tris pH 7.0/300 mM NaCl. The elution fraction was collected and can be further processed as described in example 1a.

The yield of the IgG-enriched flow-through fraction was 84%. In the IgG-enriched fraction, the IgA was below the limit of detection (<0.0116 g/L, Siemens BN Prospec) at a protein concentration of 9.81 g/L (determined by the Biuret assay). The IgM content was below the limit of detection (<0.00846 g/L). The IgG-4 subclass content was 2.31%.

The obtained IgM-enriched immunoglobulin composition had an IgM content of 28% by weight, an IgA content of 19% by weight and an IgG content of 53% by weight based on the total immunoglobulin content, at an immunoglobulin concentration of 50 mg/ml.

Example 3

Preparation of an IgG-Enriched Immunoglobulin Composition in Flow-Through Mode (Cation Exchange Chromatography)

The IgG-enriched immunoglobulin composition collected as the flow through fraction of the macroporous anion exchange chromatography (POROS® 50 HQ) in Example 1a was adjusted to pH 5.5 and to a conductivity of 22-26 mS/cm with sodium acetate buffer and NaCl and then was further purified by cation exchange chromatography in a flow-through mode on a cation exchange resin (POROS® 50 HS). The binding capacity of this resin is defined as 100-3000 g/l, and chromatography was carried out at a load of 3000 g/l and a flow-rate of 800 cm/h.

The cation exchange column was equilibrated with acetate buffer solution (pH 5.5, adjusted to 22, 24 and 26 mS/cm with NaCl). The protein solution was loaded to the column and washed with acetate buffer (pH 5.5, adjusted to 22-26 mS/cm with NaCl). The flow through fraction and the wash are collected and further processed. The residual protein is eluted with 1.5 M NaCl.

The resulting protein solution was further processed by a nanofiltration step, in order to remove potentially present virus. A Planova BioEx 20 nm filter (Asahi Kasei) was used as a virus filter. More than 50 kg of the protein solution were filtered over a 0.1 m² filter area at a protein concentration of 10 g/l. The maximum pressure was set according to the manufacturer's instructions. Flow rate during nanofiltration was as follows:

| Material after POROS 50 HS chromatography | Mean flow-rate during nanofiltration [kg/(m²*h)] |
| --- | --- |
| 22 mS/cm and pH 5.5 | 48.4 |
| 24 mS/cm and pH 5.5 | 53.0 |
| 26 mS/cm and pH 5.5 | 53.9 |

The resulting protein solution was subjected to a concentration step to >100 g/L by ultrafiltration and diafiltered into formulation buffer (0.3 M Glycine pH 5.0). The resulting protein solution was filtered through a 0.2 μm filter in order to control sterility.

The obtained immunoglobulin compositions were analysed for immunoglobulin contents, subclass distribution and ACA, and the results are shown in Table 1.

TABLE 1

Analytical parameters for drug substances produced at lab-scale

| Parameters | POROS ® 50 HS at 22 mS/cm | POROS ® 50 HS at 24 mS/cm | POROS ® 50 HS at 26 mS/cm |
| --- | --- | --- | --- |
| IgG [%] | 99.6 | 99.7 | 99.6 |
| IgA [%] | 0.26 | 0.21 | 0.24 |
| IgM [%] | 0.15 | 0.11 | 0.13 |
| IgG$_1$ [%] | 62.68 | 63.52 | 63.47 |
| IgG$_2$ [%] | 32.96 | 31.84 | 32.19 |
| IgG$_3$ [%] | 2.58 | 2.40 | 2.53 |
| IgG$_4$ [%] | 1.79 | 2.25 | 1.80 |
| ACA [CH50/mg] | 0.56 | 0.60 | 0.58 |

The drug substances obtained after the POROS® 50 HS chromatography showed ACA levels in the desired range. The ratio of IgG, IgA and IgM and subclass distribution was not changed by the additional POROS® 50 HS chromatography. The subsequent nanofiltration was inconspicuous.

Example 4

Investigation of Properdin Content in IgG Preparations with and without Cationic Exchange Chromatography In order to investigate the effect of cationic exchange chromatography step on the properdin levels in IgG preparations, four batches of Cohn fraction I/II/III obtained from pooled blood plasma were resuspended in 0.1 M sodium acetate buffer (pH 4.8) at manufacturing scale (100 kg of fraction I/II/III employed) and subjected to treatment with octanoic acid, tri-calcium phosphate, ultra-diafiltration, mild acid treatment and anion exchange chromatography as described in Example 1a. The flow through (IgG fractions) of batches 1 and 2 was collected and immediately subjected to ultra-/diafiltration versus 0.3 M glycine buffer, pH 4.6. The flow through of batches 3 and 4 was further subjected to cation exchange chromatography (CEX) as described in Example 3, and the flow-through was subjected to ultra-/diafiltration as above. All IgG solutions thus obtained were analysed for immunoglobulin and properdin content using a solid phase human properdin ELISA kit (Hycult Biotech) as described before. The results are shown in Table 2.

TABLE 2

| Sample | Immuno-globulin conc. [g/l] | Properdin conc. [μg/ml] | Properdin content per mg Immunoglobulin [μg/mg] |
| --- | --- | --- | --- |
| Batch 1 (without CEX) | 126 | 229 | 1.82 |
| Batch 2 (without CEX) | 116 | 198 | 1.71 |
| Batch 3 (with CEX) | 113 | 0.23 | 0.0020 |
| Batch 4 (with CEX) | 126 | 0.14 | 0.0011 |

As shown in Table 2, cation exchange chromatography results in an enormous reduction in properdin content.

Example 5

Determination of Properdin Content and IgG Polymer Content in IgG-Enriched Immunoglobulin Compositions IgG preparations of the invention as described in Example 4 (Batches 3 and 4) were further tested for IgG polymer content by HPSEC as described before. Properdin and IgG polymer contents of commercially available pharmaceutical IgG compositions (CP-IgG 1 to 5) were determined by the same methods for comparison. The results are shown in Table 3.

TABLE 3

| Sample | Immunoglobulin concentration [g/l] | Properdin [µg/ml] | Properdin [µg/mg] Immunoglobulin | IgG Polymer content [%] |
|---|---|---|---|---|
| Batch 3 | 113 | 0.23 | 0.0020 | 0.0 |
| Batch 4 | 126 | 0.14 | 0.0011 | 0.0 |
| CP-IgG 1 | 100 | 1.16 | 0.0116 | 0.0 |
| CP-IgG 2 | 100 | 5.11 | 0.0511 | 0.1 |
| CP-IgG 3 | 100 | 13.50 | 0.1350 | 0.6 |
| CP-IgG 4 | 100 | 4.00 | 0.0400 | 0.1 |
| CP-IgG 5 (pasteurized) | 100 | 0.04 | 0.0004 | 0.2 |

As may be seen from Table 3, IgG-enriched immunoglobulin compositions obtained according to the method of the invention have a properdin content which is below that of the commercially available pharmaceutical products except for CP-IgG 5 which is a pasteurized product. Likewise, the content of IgG polymers in the IgG-enriched immunoglobulin compositions of the invention was below that of all pharmaceutical IgG compositions except for CP-IgG 1.

Example 6

Determination of Thrombogenic Activity (TGA), Factor XIa and Factor XI (FXI) in IgG-Enriched Immunoglobulin Compositions IgG-enriched immunoglobulin compositions (3 batches) obtained as described in Example 4 after cation exchange chromatography were tested for TGA, FXIa and FX as described before using commercially available assays (Batches 5 to 7). The results are shown in Table 4.

TABLE 4

| Sample | Protein concentration [g/l] | TGA [mU/ml] | FXIa [mU/ml] | FXI [% of norm] | Purity of Ig-fraction by CZE [%] |
|---|---|---|---|---|---|
| Batch 5 | 100 | <1.5 | <2.0 | <1 | 100 |
| Batch 6 | 99 | <1.5 | <2.0 | <1 | 100 |
| Batch 7 | 99 | <1.5 | <2.0 | <1 | 100 |

The results show no residual TGA, FXIa and FXI (below detection limit of applied method).

Example 7

Long-Term Stability of IgG-Enriched Immunoglobulin Compositions

An IgG-enriched immunoglobulin composition obtained as described in Example 4 after cation exchange chromatography (118 g immunoglobulin/l) was tested for long-term stability at 5° C. and 25° C., respectively over a period of 90 weeks using HPSEC as described above. The results are shown in Table 5.

TABLE 5

Long-term stability of IgG-enriched immunoglobulin compositions

| Weeks | Polymer (%) after Storage at 5° C. | Polymer (%) after Storage at 25° C. |
|---|---|---|
| 0 | 0.0 | 0.0 |
| 1 | 0.0 | 0.0 |
| 4 | 0.0 | 0.0 |
| 8 | 0.0 | 0.0 |
| 24 | 0.0 | 0.0 |
| 65 | 0.0 | 0.5 |
| 90 | 0.0 | 0.6 |

As may be seen from the results, no IgG polymers were detectable after storage at 5° C. over a period of 90 weeks. After storage at 25° C. the polymer content of IgG remains below 1.0% after a period of 90 weeks.

Example 8

Preparation of an IgG-Enriched Immunoglobulin Composition in Binding Mode (Cation Exchange Chromatography)

An IgG fraction obtained as described in Example 1a as a flow-through from POROS® 50 HQ anion exchange chromatography was ultra/diafiltered to 20 mM sodium acetate, pH 5.5, so as to prepare the material for cation exchange chromatography with POROS® 50 HS in a binding mode.

The prepared material was successfully bound to POROS® 50 HS, and an IgG fraction was eluted with buffer (20 mM sodium acetate, 225 mM sodium chloride, pH 5.5±0.1, conductivity 24±2 mS/cm). The obtained IgG-enriched immunoglobulin composition had an ACA value of 0.58 CH50/mg protein.

Example 9

ACA Break-Through Curves at Different Conductivities (Cation Exchange Chromatography)

IgG fractions obtained as described in Example 1a as a flow-through from POROS® 50 HQ anion exchange chromatography were ultra/diafiltered to 10 mM Tris, 6.5 mM sodium acetate and adjusted to pH 5.5 and conductivities of 22, 24 and 26 mS/cm using NaCl. ACA break-through curves were obtained using a POROS® 50 HS column with a column volume of 0.8 ml. The protein solution was pumped over the POROS® 50 HS column at a flow-rate of 800 cm/h to remove ACA.

Table 6 shows the results obtained for ACA-breakthrough at the intended conductivities. In all cases ACA is efficiently removed up to a load of at least 3 g protein/ml gel. The ACA levels rise again with higher loads. The higher the conductivity the faster the ACA levels rise.

TABLE 6

ACA-break-through at 22, 24 and 26 mS/cm

| Load [g protein/l gel] | Protein concentration [g/l] | ACA [CH50/mg] |
|---|---|---|
| 22 mS/cm | | |
| Load material | 69.25 | 1.18 |
| 3000 | 55.35 | 0.66 |
| 4000 | 62.64 | 0.74 |
| 5000 | 63.10 | 0.78 |
| 6000 | 59.69 | 0.78 |
| 7000 | 61.70 | 0.88 |
| 8000 | 62.03 | 0.90 |

TABLE 6-continued

ACA-break-through at 22, 24 and 26 mS/cm

| Load [g protein/l gel] | Protein concentration [g/l] | ACA [CH50/mg] |
|---|---|---|
| 24 mS/cm | | |
| Load material | 70.65 | 1.06 |
| 3000 | 54.95 | 0.66 |
| 4000 | 61.16 | 0.90 |
| 5000 | 60.11 | 0.88 |
| 6000 | 58.90 | 0.90 |
| 7000 | 59.56 | 1.02 |
| 8000 | 60.56 | 0.98 |
| 26 mS/cm | | |
| Load material | 65.50 | 1.20 |
| 3000 | 56.42 | 0.78 |
| 4000 | 62.57 | 0.92 |
| 5000 | 59.42 | 0.98 |
| 6000 | 59.03 | 1.02 |
| 7000 | 60.36 | 1.04 |
| 8000 | 57.82 | 1.06 |

Example 10

Variation of Conductivity (Cation Exchange Chromatography)

IgG fractions obtained as in Example 1a as a flow-through from POROS® 50 HQ anion exchange chromatography were adjusted to pH of 5.5 and conductivities ranging from 16 to 30 mS/cm using 20 mM Na acetate buffer and NaCl. The thus prepared material was applied to a POROS® 50 HS column (column load 500 g/l), and fractions were collected and the ACA level was determined. The results are shown in Table 7.

TABLE 7

ACA values with variation of conductivity settings

| Conductivity settings [mS/cm] | ACA [CH50/mg protein] |
|---|---|
| Before POROS ® 50 HS | 1.30 |
| 16 | 0.53 |
| 18 | 0.52 |
| 20 | 0.48 |
| 22 | 0.45 |
| 24 | 0.49 |
| 26 | 0.43 |
| 28 | 0.44 |
| 30 | 0.50 |

A reduction of ACA levels could be realized over a wide range of conductivity settings. Lower conductivities have a risk of loss of IgG yield and higher conductivities have a risk of ACA break-through.

Example 11

Variation of Flow Rates (Cation Exchange Chromatography)

IgG fractions obtained as described in Example 1a as a flow-through from POROS® 50 HQ anion exchange chromatography were ultra/diafiltrated to 10 mM Tris, 6.5 mM sodium acetate, 225 mM sodium chloride (pH 5.5; conductivity 22 mS/cm). The thus prepared material was applied to a POROS® 50 HS column at 200, 500 and 800 cm/h (load 1.2 g/ml POROS® 50 HS). The flow-through fractions were collected and the ACA level was determined. The results are shown in Table 8.

TABLE 8

ACA values with variation of flow rate during POROS ® 50 HS chromatography

| Flow-rate [cm/h] | ACA [CH50/mg] |
|---|---|
| Before POROS ® 50 HS chromatography | 1.12 |
| 200 | 0.62 |
| 500 | 0.66 |
| 800 | 0.62 |

As may be seen from Table 8, flow-rates have no significant effect on ACA.

Example 12

Membrane Adsorber as Cation Exchange Material

Depletion of ACA in an IgG-enriched immunoglobulin composition obtained as described in Example 1a as a flow-through from POROS® 50 HQ anion exchange chromatography was tested using a cationic membrane adsorber (Sartorius-Sartobind S) in a non-binding mode for IgG. The IgG-enriched solution was adjusted to a pH of 5.5 using a sodium acetate buffer and a sodium chloride concentration of 225 mM (corresponding to a conductivity of 24 mS/cm). Under these conditions IgG does not bind to the cation exchange material. The membrane adsorber module was loaded with 0.5 g/ml resin. The flow-through fraction and a high-salt elution fraction (1.5 M NaCl) were collected and analyzed for ACA. The ACA value of the flow-through fraction is low (CH50/mg=0.44), whereas the bound fraction is enriched in its ACA content (CH50/mg >1.5).

Example 13

Use of Cation Exchange Resin in Batch Mode

An IgG-enriched immunoglobulin composition obtained as described in Example 1a as a flow-through from POROS® 50 HQ anion exchange chromatography was ultra/diafiltrated to 10 mM Tris, 6.5 mM sodium acetate, 225 mM sodium chloride (pH 5.5; conductivity 21 mS/cm) and adjusted to a protein content of 50 g/l. POROS 50 HS chromatography material was added as a powder and the suspension was gently shaken for 1 hour at room temperature. The following amounts of POROS 50 HS were thus tested in a batch mode and the results are shown in Table 9.

TABLE 9

Use of POROS ® 50 HS in batch mode

| Protein load [mg POROS ® 50 HS/g Protein] | ACA [CH50/mg protein] |
|---|---|
| Starting material | 1.12 |
| 100 | 0.98 |
| 250 | 0.70 |
| 500 | 0.52 |

ACA could successfully be removed below 1 CH50/mg at load conditions of greater than 250 mg POROS® 50 HS/g protein.

Example 14

Properdin Spike Experiments

In order to demonstrate the correlation between properdin content and ACA, a 1 mg/ml properdin solution (obtained from Quidel) was spiked into two different 10% IgG-immunoglobulin (IVIg preparations A and B) that had been processed using a cation exchange chromatography for polishing and ACA was measured. As shown in Table 10, increasing concentrations of properdin lead to an increase in ACA in a linear dependency up to concentrations of a properdin spike of 200 µg/ml.

TABLE 10

ACA in Properdin spiked immunoglobulin solution

| Properdin spike [µg/ml] | IgG preparation A ACA [CH50/mg] | IgG preparation B [CH50/mg] |
|---|---|---|
| 0 | 0.42 | 0.42 |
| 25 | 0.52 | 0.60 |
| 50 | 0.58 | 0.70 |
| 100 | 0.82 | 0.92 |
| 150 | 0.94 | 1.10 |
| 200 | 1.08 | 1.16 |

Example 15

Effect of Resolubilization Buffer on Properdin Content After Octanoic Acid Treatment.

In order to demonstrate the correlation between conditions for resolubilization and properdin content after octanoic acid treatment, Cohn fraction I/II/III was resuspended in deionized water and three different resolubilization buffers. The suspensions of fraction I/II/III were subjected to treatment with octanoic acid (pH 4.8, 17.5 g/kg octanoic acid per kg suspension) and tri-calcium phosphate, as outlined in Example 1a. The precipitate was removed by depth filtration, and the resulting protein solution was subjected to ultra-/diafiltration and mild acid treatment at pH 4. The impurity depleted immunoglobulin composition thus obtained was analyzed for the properdin content. The results are shown in Table 11.

TABLE 11

| Sample | Condition | Conductivity (at 22° C.) mS/cm | Protein conc. [g/l] | Properdin concentration [µg/ml] | Properdin content per mg protein [µg/mg] |
|---|---|---|---|---|---|
| 1 | Deiononized water | 0.09 | 46.8 | 5 | 0.107 |
| 2 | 10 mM sodium acetate buffer, pH 4.8 | 0.77 | 46.8 | 11 | 0.235 |
| 3 | 50 mM sodium acetate buffer, pH 4.8 | 2.6 | 42.5 | 36 | 0.847 |
| 4 | 100 mM sodium acetate buffer, pH 4.8 | 6.9 | 44.6 | 42 | 0.941 |

As may be seen from the results, the properdin content in the immunoglobulin compositions obtained after octanoic acid treatment increases with increasing molarity of the resolubilization buffer.

Example 16

Effect of Resolubilization Buffer on Properdin Content in IgG-Enriched Immunoglobulin Compositions Obtained After Anion Exchange Chromatography In order to investigate the effect of the resolubilization buffer on the properdin content in IgG preparations obtained after anion exchange chromatography, Cohn fraction I/II/III was resuspended in either Water for Injection (WFI) or 100 mM sodium acetate buffer (pH 4.8) at laboratory scale in a fraction I/II/II to buffer ratio of 1:4. Both suspensions were treated with octanoic acid and tri-calcium phosphate, followed by ultra-diafiltration and mild acid treatment at pH 4 as described in Example 13. The resulting immunoglobulin compositions were subjected to anionic exchange chromatography on POROS 50 HQ as described in Example 1a, and the resulting flow-through fraction (IgG-enriched fraction) was subjected to ultra-/diafiltration versus 0.3 M glycine buffer, pH 4.6.

The resulting IgG solutions were analysed for the protein and properdin content, and the results are shown in Table 12.

TABLE 12

| Sample | Immuno-globulin conc. | Properdin conc. [µg/ml] | Properdin content per mg Immuno-globulin [µg/mg] | ACA [CH50/mg] |
|---|---|---|---|---|
| Cohn fraction I/II/III resuspended in WFI | 97 | 0.27 | 0.003 | 0.77 |
| Cohn fraction I/II/III resuspended in 100 mM sodium acetate buffer, pH 4.8 | 128 | 214 | 1.67 | 1.18 |

Example 17

Effect of WFI and Acetate Buffer on Suspensions of Cohn Fraction I/II/III

Fraction I/II/III was resuspended at laboratory scale either in WFI (Sample A) or in 100 mM sodium acetate buffer (pH 4.8; Sample B) at a weight ratio of fraction I/II/II to buffer of 1:4 (300 g of fraction I/II/III plus 1200 g of buffer or WFI). The concentrations of IgG, IgA and IgM in the suspension as well as the distribution between the immunoglobulin classes were determined. The results are shown in Table 13.

TABLE 13

Effect of buffer on resolubilization of immunoglobulin from Cohn fraction I/II/II

| Sample | IgG [g/l] | IgA [g/l] | IgM [g/l] | Sum IgG, IgA, IgM [g/l] | IgG [%] | IgA [%] | IgM [%] |
|---|---|---|---|---|---|---|---|
| A | 18.0 | 1.9 | 0.69 | 20.6 | 87.3 | 9.3 | 3.4 |
| B | 19.1 | 2.9 | 2.05 | 24.0 | 79.2 | 12.2 | 8.5 |

The concentrations of IgG, IgA and IgM in the sample resuspended in acetate buffer (sample B) increase compared to the sample resuspended in WFI (sample A). The IgM concentration raises from 0.69 g/l to 2.05 g/l; the IgA concentration is elevated from 1.9 g/l to 2.9 g/l in the suspension samples.

The yields for the individual immunoglobulin classes were calculated, based on the suspension volume achieved (1500 ml) and in respect to the amount of fraction I/II/III employed. An increase in yield of 7% for IgG, 51% for IgA and 212% for IgM was observed for the suspension in acetate. The results are shown in Table 14.

TABLE 14

Effect of buffer on immunoglobulin yields in suspension

| Sample | IgG [g] | IgA [g] | IgM [g] | IgG per kg fraction I/II/III [g/kg] | IgA per kg fraction I/II/III [g/kg] | IgM per kg fraction I/II/III [g/kg] |
|---|---|---|---|---|---|---|
| A | 27.0 | 2.9 | 1.0 | 90 | 9.7 | 3.3 |
| B | 28.7 | 4.4 | 3.1 | 96 | 14.7 | 10.3 |

The invention claimed is:

1. A process for the preparation of a pharmaceutically acceptable immunoglobulin composition[s] from a plasma-derived immunoglobulin fraction comprising or consisting of Cohn fraction I/II/III or Kistler-Nitschmann fraction A+I, said process comprising the steps of:
    (a) resolubilizing immunoglobulin contained in the plasma-derived immunoglobulin fraction comprising or consisting of Cohn fraction I/II/III or Kistler-Nitschmann fraction A+I by resuspending said plasma-derived immunoglobulin fraction under conditions to adjust the conductivity of the suspension to at least 1 mS/cm to obtain a suspension containing resolubilized IgG, IgM and IgA;
    (b) precipitating contaminating protein in the suspension obtained in step (a) and removing said contaminating protein to obtain an impurity-depleted immunoglobulin composition;
    (c) subjecting the impurity depleted immunoglobulin composition obtained in step (b) to ion exchange chromatography using an anion exchange resin under conditions of pH and conductivity adjusted to substantially bind IgM and IgA to the resin, and obtaining an IgG-enriched immunoglobulin composition in the flow-through fraction and/or by eluting IgG from the anion exchange resin under conditions where IgM and IgA remain bound to the anion exchange resin; and
    (d) subjecting contacting the IgG-enriched immunoglobulin composition obtained in step (c) to treatment with a cation exchange material under conditions of pH and conductivity where properdin is bound to said cation exchange material, comprising contacting the IgG-enriched immunoglobulin composition with said cation exchange material at a pH in the range of from 5.0 to 6.0 and at a conductivity in the range of from 16 to 30 mS/cm, and recovering IgG to obtain an IgG-enriched immunoglobulin composition having a reduced properdin content.

2. The process of claim 1 comprising the steps of:
    (a) resolubilizing immunoglobulin contained in the plasma-derived immunoglobulin fraction comprising or consisting of Cohn fraction I/II/III or Kistler-Nitschmann fraction A+I by resuspending said plasma-derived immunoglobulin fraction under conditions to adjust the conductivity of the suspension to at least 1 mS/cm to obtain a suspension containing resolubilized IgG, IgM and IgA;
    (b) precipitating contaminating protein in the suspension obtained in step (a) and removing said contaminating protein to obtain an impurity-depleted immunoglobulin composition, wherein precipitating contaminating protein comprises treating the suspension obtained in step (a) with octanoic acid;
    (c) subjecting the impurity depleted immunoglobulin composition obtained in step (b) to ion exchange chromatography using an anion exchange resin under conditions of pH and conductivity adjusted to bind, based on the amount of each immunoglobulin subjected to ion exchange chromatography, at least 90% by weight of each of IgM and IgA to the resin, and obtaining an IgG-enriched immunoglobulin composition[s] in the flow-through fraction and/or by eluting IgG from the anion exchange resin under conditions where IgM and IgA remain bound to the anion exchange resin; and
    (d) subjecting the IgG-enriched immunoglobulin composition obtained in step (c) to treatment with a cation exchange material under conditions of pH and conductivity where properdin is bound to said cation exchange material, comprising contacting the IgG-enriched immunoglobulin composition with said cation exchange material at a pH in the range of from 5.0 to 6.0 and at a conductivity in the range of from 16 to 30 mS/cm, and recovering IgG to obtain an IgG-enriched immunoglobulin composition having a reduced properdin content.

3. The process of claim 1, wherein step (c) further comprises using an anion exchange resin under conditions of pH and conductivity adjusted to also bind IgG to the resin.

4. The process of claim 2, wherein step (c) further comprises using an anion exchange resin under conditions of pH and conductivity adjusted to also bind IgG to the resin.

5. The process of claim 1, wherein the conductivity of the suspension is at least 1.5 mS/cm.

6. The process of claim 1, wherein resuspending of the plasma-derived immunoglobulin fraction is carried out using a buffer adjusted to a pH in the range of from 4.2 to 5.5.

7. The process of claim 6, wherein the buffer is an acetate buffer.

8. The process of claim 1, wherein precipitating contaminating protein in step (b) comprises treating the suspension obtained in step (a) with octanoic acid.

9. The process of claim 1, wherein removing contaminating protein in step (b) comprises filtration.

10. The process of claim 1, wherein step (b), following removal of contaminating protein, further includes subjecting the impurity-depleted immunoglobulin composition to a mild acid treatment, wherein the immunoglobulin composition is incubated at a pH in the range of from 3.8 to 4.5 before subjecting it to ion exchange chromatography with an anion exchange resin in step (c).

11. The process of claim 10, wherein step (b), following removal of contaminating protein, further includes subjecting the impurity-depleted immunoglobulin composition to a mild acid treatment, wherein the immunoglobulin composition is incubated at a temperature in the range of from 35 to 40° C. before subjecting it to ion exchange chromatography with an anion exchange resin in step (c).

12. The process of claim 1, wherein the anion exchange resin used in step (c) is a macroporous anion exchange resin.

13. The process of claim 12, wherein the anion exchange chromatography is carried out at a pH in the range of from 6.7 to 7.5.

14. The process of claim 12, wherein the anion exchange chromatography is carried out at a conductivity in the range of from 4 to 7.5 mS/cm.

15. The process of claim 12, wherein IgM and/or IgA bound to the anion exchange resin are eluted from the resin at a conductivity of at least 20 mS/cm.

16. The process of claim 15, wherein elution is carried out at a pH in the range of from 6.7 to 7.5.

17. The process of claim 1, wherein treatment of the IgG-enriched immunoglobulin composition in step (d) is carried out by contacting the IgG-enriched immunoglobulin composition with a cationic membrane adsorber under conditions of pH and conductivity where properdin is bound to the cationic membrane adsorber and IgG is recovered in the flow-through fraction.

18. The process of claim 1, wherein treatment in step (d) is carried out by contacting the IgG-enriched immunoglobulin composition with the cation exchange material at a pH in the range of from 5.2 to 5.8.

19. The process of claim 18, wherein treatment in step (d) is carried out by contacting the IgG-enriched immunoglobulin composition with the cation exchange material at a conductivity in the range of from 20 to 28 mS/cm.

20. The process of claim 1, wherein step (c) further comprises eluting from the anion exchange resin IgM and/or IgA to obtain an immunoglobulin composition enriched in IgM and/or IgA.

21. The process of claim 20, further comprising subjecting the IgG-enriched immunoglobulin composition obtained in step (d) and/or the immunoglobulin composition enriched in IgM and/or IgA obtained in step (c) to further treatment for virus inactivation to obtain a virus inactivated preparation.

22. The process of claim 20, further comprising the step of formulating the IgG-enriched immunoglobulin composition obtained in step (d) and/or the immunoglobulin composition enriched in IgM- and/or IgA obtained in step (c) into a pharmaceutical preparation.

23. A process for reducing the properdin content in a properdin-containing IgG composition, said process comprising subjecting said properdin-containing IgG composition to treatment with a cation exchange material under conditions of pH and conductivity where properdin is bound to said cation exchange material to obtain an IgG composition having a reduced properdin content, wherein treatment is carried out by contacting the IgG composition with the cation exchange material at a pH in the range of from 5.0 to 6.0 and at a conductivity in the range of from 16 to 30 mS/cm.

24. The process of claim 23, wherein treatment with the cation exchange material is carried out by subjecting the properdin-containing IgG composition to cation exchange chromatography under conditions where properdin is bound to said cation exchange material and IgG is recovered in the flow-through fraction.

25. The process of claim 23, wherein treatment of the IgG-enriched immunoglobulin composition is carried out by contacting the IgG-enriched immunoglobulin composition with a cationic membrane adsorber under conditions where properdin is bound to the cationic membrane adsorber and IgG is recovered in the flow-through fraction.

26. The process of claim 23, wherein treatment is carried out by contacting the IgG composition with the cation exchange material at a pH in the range of from 5.2 to 5.8.

27. The process of claim 23, wherein treatment is carried out by contacting the IgG composition with the cation exchange material at a conductivity in the range of from 20 to 28 mS/cm.

28. The process of claim 23, wherein the properdin-containing IgG composition is an IgG-enriched immunoglobulin composition, said IgG-enriched immunoglobulin composition having an IgG content of at least 95% by weight, based on the total weight of immunoglobulin in the properdin-containing IgG composition.

29. A process for reducing the anticomplementary activity (ACA) of a properdin-containing IgG composition by reducing the properdin content thereof, said process comprising subjecting said properdin-containing IgG composition to treatment with a cation exchange material under conditions of pH and conductivity where properdin is bound to said cation exchange material to obtain an IgG composition having a reduced ACA and properdin content, wherein treatment is carried out by contacting the IgG composition with the cation exchange material at a pH in the range of from 5.0 to 6.0 and at a conductivity in the range of from 16 to 30 mS/cm.

* * * * *